US010012629B2

(12) United States Patent
Suzuki et al.

(10) Patent No.: US 10,012,629 B2
(45) Date of Patent: Jul. 3, 2018

(54) GAS MONITORING SYSTEM AND GAS MONITORING METHOD

(71) Applicant: HONDA MOTOR CO., LTD., Tokyo (JP)

(72) Inventors: Akihiro Suzuki, Utsunomiya (JP); Takashi Kawaura, Sakura (JP)

(73) Assignee: HONDA MOTOR CO., LTD., Tokyo (JP)

( * ) Notice: Subject to any disclaimer, the term of this patent is extended or adjusted under 35 U.S.C. 154(b) by 440 days.

(21) Appl. No.: 14/691,975

(22) Filed: Apr. 21, 2015

(65) Prior Publication Data
US 2015/0308998 A1 Oct. 29, 2015

(30) Foreign Application Priority Data

Apr. 25, 2014 (JP) ................. 2014-090871

(51) Int. Cl.
*G01M 3/00* (2006.01)
*G01N 33/00* (2006.01)
*B60L 11/18* (2006.01)

(52) U.S. Cl.
CPC ...... *G01N 33/0027* (2013.01); *B60L 11/1881* (2013.01); *G01M 3/00* (2013.01)

(58) Field of Classification Search
CPC .... G01M 3/007; G01M 3/00; G01N 33/0036; G01N 33/0027; G08B 21/14; G08B 21/16; G06F 13/4086; H04L 12/40006; H04L 2012/40215; H04L 2012/40273; B60L 11/1811
See application file for complete search history.

(56) References Cited

U.S. PATENT DOCUMENTS 8,962,207 B2   2/2015   Kajiwara et al.
2003/0204337 A1  10/2003   Beutelschiess
(Continued)

FOREIGN PATENT DOCUMENTS

DE   112008002706 T5   8/2010
DE   102014208643 A1   12/2014
(Continued)

OTHER PUBLICATIONS

German Office Action and Search Report application No. 102015207304.1 dated Sep. 8, 2016.
(Continued)

*Primary Examiner* — Blake A Tankersley
(74) *Attorney, Agent, or Firm* — Squire Patton Boggs (US) LLP

(57) ABSTRACT

A gas monitoring system and a gas monitoring method make it possible to identify plural gas sensors having a single specification and which are connected to one trunk line. Trunk line connectors have identification configurations for allowing information concerning positions where the trunk line connectors to be identified are arranged. Hydrogen sensors have a single specification (the same specification). When connectors of the hydrogen sensors are fitted to the trunk line connectors, the hydrogen sensors store the sensor IDs, which are assigned to the hydrogen sensors, in memory units based on the identification configurations of the trunk line connectors.

4 Claims, 12 Drawing Sheets

(56) References Cited

U.S. PATENT DOCUMENTS

| | | | |
|---|---|---|---|
| 2006/0113198 A1* | 6/2006 | Sasaki | G01N 33/007 205/775 |
| 2010/0233562 A1* | 9/2010 | Kajiwara | G01M 3/007 429/444 |
| 2014/0344499 A1 | 11/2014 | Uemura et al. | |

FOREIGN PATENT DOCUMENTS

| | | |
|---|---|---|
| JP | 2003-149071 A | 5/2003 |
| JP | 2006-071413 A | 3/2006 |
| JP | 2006-140132 A | 6/2006 |
| JP | 2007-126055 A | 5/2007 |
| JP | 2009-092528 A | 4/2009 |

OTHER PUBLICATIONS

Japanese Office Action application No. 2014-090871 dated Dec. 20, 2016.

* cited by examiner

FIG. 6

| POSITION-CORRESPONDING UNIQUE ID | | SENSOR UNIQUE ID |
|---|---|---|
| TRUNK LINE SIDE BRANCH LINE ASSEMBLY | HYDROGEN SENSOR | |
| VEHICLE HARNESS SPECIFICATION | HYDROGEN SENSOR SPECIFICATION | |
| CAN-ID5<br>POWER SUPPLY — 175 — Sw<br>GND / CAN-H / CAN-L / ID A / ID B / ID C / ID D<br>105 | GND / CAN-H / CAN-L / ID A / ID B / ID C / ID D — 205s HYDROGEN SENSOR 205m<br>205  154 | POWER SUPPLY<br>SENSOR ID5 |
| CAN-ID6<br>POWER SUPPLY — 176 — Sw<br>GND / CAN-H / CAN-L / ID A / ID B / ID C / ID D<br>106 | GND / CAN-H / CAN-L / ID A / ID B / ID C / ID D — 206s HYDROGEN SENSOR 206m<br>206  155 | POWER SUPPLY<br>SENSOR ID6 |
| CAN-ID7<br>POWER SUPPLY — 177 — Sw<br>GND / CAN-H / CAN-L / ID A / ID B / ID C / ID D<br>107 | GND / CAN-H / CAN-L / ID A / ID B / ID C / ID D — 207s HYDROGEN SENSOR 207m<br>207  156 | POWER SUPPLY<br>SENSOR ID7 |
| CAN-ID8<br>POWER SUPPLY — 178 — Sw<br>GND / CAN-H / CAN-L / ID A / ID B / ID C / ID D<br>108 | GND / CAN-H / CAN-L / ID A / ID B / ID C / ID D — 208s HYDROGEN SENSOR 208m<br>208  157 | POWER SUPPLY<br>SENSOR ID8 |

FIG. 9

| POSITION-CORRESPONDING UNIQUE ID | | SENSOR UNIQUE ID |
|---|---|---|
| TRUNK LINE SIDE BRANCH LINE ASSEMBLY | HYDROGEN SENSOR | |
| VEHICLE HARNESS SPECIFICATION | HYDROGEN SENSOR SPECIFICATION | |
| LIN-ID1 — POWER SUPPLY, 301, Sw, GND, LIN, ID A, ID B (311) | 401, 221 — GND, LIN, ID A, ID B, 221s HYDROGEN SENSOR, 221m | POWER SUPPLY, SENSOR ID1 |
| LIN-ID2 — POWER SUPPLY, 302, Sw, GND, LIN, ID A, ID B (312) | 402, 222 — GND, LIN, ID A, ID B, 222s HYDROGEN SENSOR, 222m | POWER SUPPLY, SENSOR ID2 |
| LIN-ID3 — POWER SUPPLY, 303, Sw, GND, LIN, ID A, ID B (313) | 403, 223 — GND, LIN, ID A, ID B, 223s HYDROGEN SENSOR, 223m | POWER SUPPLY, SENSOR ID3 |
| LIN-ID4 — POWER SUPPLY, 304, GND, LIN, ID A, ID B (314) | 404, 224 — GND, LIN, ID A, ID B, 224s HYDROGEN SENSOR, 224m | POWER SUPPLY, SENSOR ID4 |

GAS MONITORING SYSTEM AND GAS MONITORING METHOD

CROSS-REFERENCE TO RELATED APPLICATION

This application is based upon and claims the benefit of priority from Japanese Patent Application No. 2014-090871 filed on Apr. 25, 2014, the contents of which are incorporated herein by reference.

BACKGROUND OF THE INVENTION

Field of the Invention

The present invention relates to a gas monitoring system using a plurality of gas sensors (e.g., hydrogen sensors), and further relates to a gas monitoring system and a gas monitoring method that can be applied suitably to a fuel cell vehicle, etc.

Description of the Related Art

In recent years, green wave activities have been proposed, e.g., from the standpoint of reducing $CO_2$ emissions, etc. To this end, environmentally friendly fuel cell vehicles are drawing attention.

In Japanese Laid-Open Patent Publication No. 2006-071413 (hereinafter referred to as JP2006-071413A), in relation to a fuel cell vehicle equipped with a fuel cell system, the necessity of detecting hydrogen concentration (gas concentration) at a plurality of positions within the vehicle is described.

In the fuel cell vehicle disclosed in JP2006-071413A, at each of respective gas detection positions, a lower end (open front end) side is provided for each gas channel, and an upper end side of each gas channel extends to an inlet port of a channel switching device such as a rotary valve. An outlet port of the channel switching device is connected to a detection channel at which one hydrogen sensor and a suction pump are provided (paragraph of JP2006-071413A, FIG. 1).

In addition, the inlet port of the channel switching device is switched successively to the outlet port. While gas is drawn in by the suction pump, the hydrogen sensor detects the hydrogen concentration in each of the gas channels (paragraph [0029] of JP2006-071413A).

Japanese Laid-Open Patent Publication No. 2003-149071 (hereinafter referred to as JP2003-149071A) discloses a gas leakage detection apparatus. In the gas leakage detection apparatus, hydrogen sensors are provided at respective gas detection positions in a fuel cell vehicle. Electric wires for transmitting signal outputs from the hydrogen sensors are wired to a control unit (paragraphs [0018], [0019] and FIG. 1 of JP2003-149071A).

SUMMARY OF THE INVENTION

However, in the technique disclosed in JP2006-071413A, since a large number of gas channels including pipes for gas leakage detection are provided in the vehicle in a complicated manner, an assembly step for this operation and substantial maintenance costs are required. Further, in the technique disclosed in JP2006-071413A, since one hydrogen sensor is switched in order to detect the hydrogen concentration at a plurality of positions, it may not be possible to detect the hydrogen concentration continuously at all times due to the switching interval of the fluid passage switching device such as the rotary valve.

In contrast, if hydrogen sensors are provided at a plurality of positions, as in the case of JP2003-149071A, although it is possible to detect the hydrogen concentration at each position at all times, as described above, each of the hydrogen sensors needs to be connected to the control device by electric wires. Therefore, the electric wiring for the vehicle becomes complex, a substantial number of steps for wiring operations are required, and substantial maintenance costs are required.

For simplifying electric wiring in the vehicle, it is preferable to implement serial communications utilizing a bus system, such as a CAN (Controller Area Network) bus or a LIN (Local Interface Network) bus.

However, in a gas monitoring system that requires a plurality of gas sensors each having the same function and which are electrically connected to a serial communication bus line (harness), such as the above-described hydrogen sensors, although in terms of component costs and component management costs, it is desirable to use gas sensors having a single specification (same external appearance, same internal structure) as standard parts (general purpose parts), a technique has not yet been established for identifying a plurality of gas sensors, each of which is connected to a bus line for carrying out serial communications.

The present invention has been made while taking into consideration the aforementioned problems. An object of the present invention is to provide a gas monitoring system and a gas monitoring method, which make it possible to identify a plurality of gas sensors having a single specification (same specification) and which are connected to one trunk line.

A gas monitoring system according to the present invention is a gas monitoring system that uses a plurality of gas sensors connected to one trunk line. The gas monitoring system includes the gas sensors having connectors and assignable to a plurality of unique IDs, trunk line connectors provided for the trunk line and a control device connected to the trunk line for controlling each of the gas sensors. The connectors of the gas sensors are fittable to the trunk line connectors. The trunk line connectors have identification configurations for allowing information concerning positions of the trunk line connectors to be identified. The gas sensors have ID setting units for assigning the unique IDs to the gas sensors based on the identification configurations of the trunk line connectors when the connectors of the gas sensors are fitted to the trunk line connectors. The control device has a gas sensor identification memory unit for storing information concerning positions of the gas sensors associated with the unique IDs of each of the gas sensors.

A gas monitoring method according to the present invention is a gas monitoring method that makes use of gas sensors equipped with connectors having a single specification, and the connectors of the gas sensors are fittable to trunk line connectors with position-corresponding unique IDs provided at plural positions of one trunk line that is connected to a control device. The method comprises the steps of, when the connectors of the gas sensors are fitted to the trunk line connectors along with the position-corresponding unique IDs, assigning unique IDs corresponding to the position-corresponding unique IDs of the trunk line connectors to the gas sensors, which are equipped with the connectors fitted to the trunk line connectors, transmitting the unique IDs, which are assigned to the gas sensors equipped with the connectors, to the control device through the trunk line, and checking the unique IDs, which are assigned to the gas sensors equipped with the connectors and are received by the control device, for matching with the position-corresponding unique IDs corresponding to position information, which is stored by the control device in correspondence with positions of the trunk line.

In the gas monitoring system and the gas monitoring method according to the present invention, it is possible to identify a plurality of gas sensors that are connected to one trunk line in order to easily obtain information concerning the positions of the gas sensors. Further, since it is possible to use gas sensors having a single specification (i.e., the same specification), management of parts or components can be performed easily. It is further possible to reduce component costs and component management costs. Moreover, erroneous assembly or assembly of mistaken components, etc., can be prevented.

Further, since the plural gas sensors are connected by the one trunk line, in a state in which information concerning each of the positions thereof can be identified, inspection at the time of completion of production can be performed easily.

In this case, the control device may generate an alarm signal when a detection value of any of the gas sensors becomes equal to or greater than an abnormal condition determination threshold, and different values may be determined as abnormal condition determination threshold values for the gas sensors based on information concerning the positions of the gas sensors. By determining the abnormal condition determination threshold values, which have different values, respectively, corresponding to the positions of the gas sensors, it is possible to generate a suitable alarm signal in correspondence with the positions of the gas sensors.

In this regard, the abnormal condition determination threshold values may be determined such that the abnormal condition determination threshold values become lower as the distance between the gas sensor and a target of leakage detection closest to the gas sensor becomes large. By providing the abnormal condition determination threshold values, which correspond with the attachment positions of the gas sensors, the abnormal condition can be determined precisely. Thus, it is possible to prevent detection of an abnormal condition in vain, and delays in detecting abnormal conditions can be avoided.

The gas monitoring system may be mounted in a fuel cell vehicle equipped with a fuel cell system. In addition, the gas monitoring method may be implemented in a fuel cell vehicle that is equipped with such a fuel cell system. In this case, the fuel cell vehicle may include at least two fuel tanks, the gas sensors may be provided above the fuel tanks, respectively, and the control device may further include a fuel supply continuation unit (fuel supply continuation step), in which, when any one of the gas sensors provided above the fuel tanks has detected an abnormal condition, the fuel supply continuation unit continues to supply fuel to a fuel cell using only the fuel tank for which the gas sensor has not detected an abnormal condition. In this manner, since by using the fuel tank for which a detected abnormal condition has not been detected, it is possible to continue operation of the fuel cell system, an improvement in merchantability of the gas monitoring system and method can be achieved.

In the present invention, information concerning the positions of the gas sensors having the single specification (i.e., the same specification), which are connected to one trunk line, can be identified (distinguished) and obtained. Further, since gas sensors having a single specification can be used, management of parts or components can be performed easily. Moreover, it is possible to prevent the occurrence of erroneous assembly or assembly of mistaken components, etc.

Further, since the plural gas sensors are connected by the one trunk line, in a state in which information concerning the positions thereof can be identified, inspection at the time of completion of production can be performed easily.

The above and other objects, features and advantages of the present invention will become more apparent from the following description when taken in conjunction with the accompanying drawings, in which a preferred embodiment of the present invention is shown by way of illustrative example.

BRIEF DESCRIPTION OF THE DRAWINGS

FIG. 6 is another connection configuration diagram of the branch line assembly having fifteen different IDs, which are assignable by changing pin positions (pole positions) at respective opposite ends of a short circuiting wire provided between the pins (between poles) of an 8-pole connector;

FIG. 9 is a connection configuration diagram of a branch line assembly having four different IDs, which are assignable by changing pin positions (pole positions) at respective opposite ends of a short circuiting wire provided between the pins (between poles) of a 5-pole connector;

DESCRIPTION OF THE PREFERRED EMBODIMENTS

Hereinafter, a preferred embodiment of a gas monitoring system according to the present invention will be described in detail below with reference to the accompanying drawings.

Figure 1A:
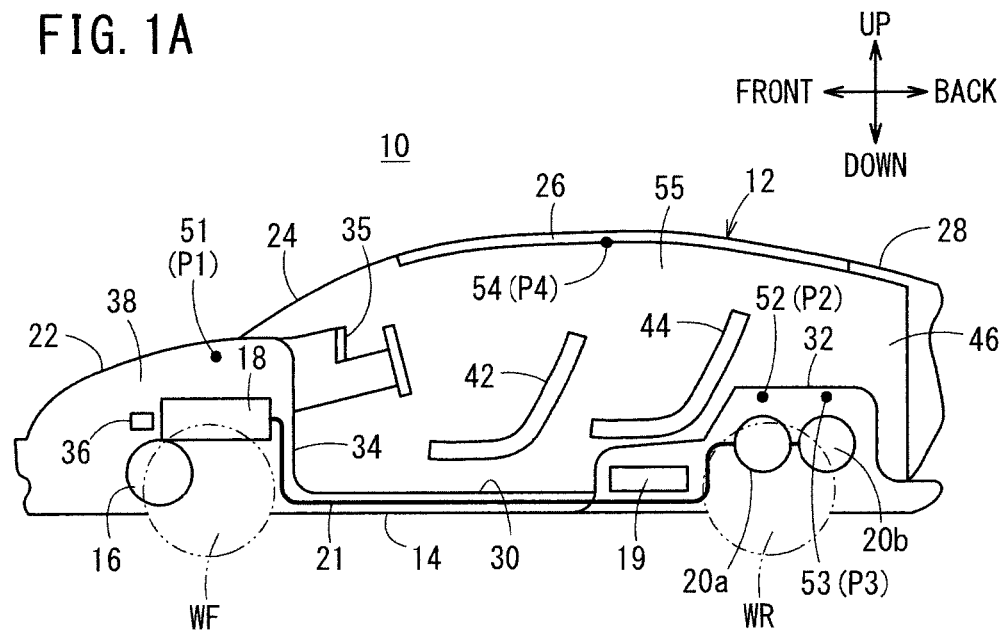
FIG. 1A is a side view schematically showing the structure of a fuel cell vehicle, which is equipped with a gas monitoring system for carrying out a gas monitoring method according to an embodiment of the present invention.
Figure 1B:
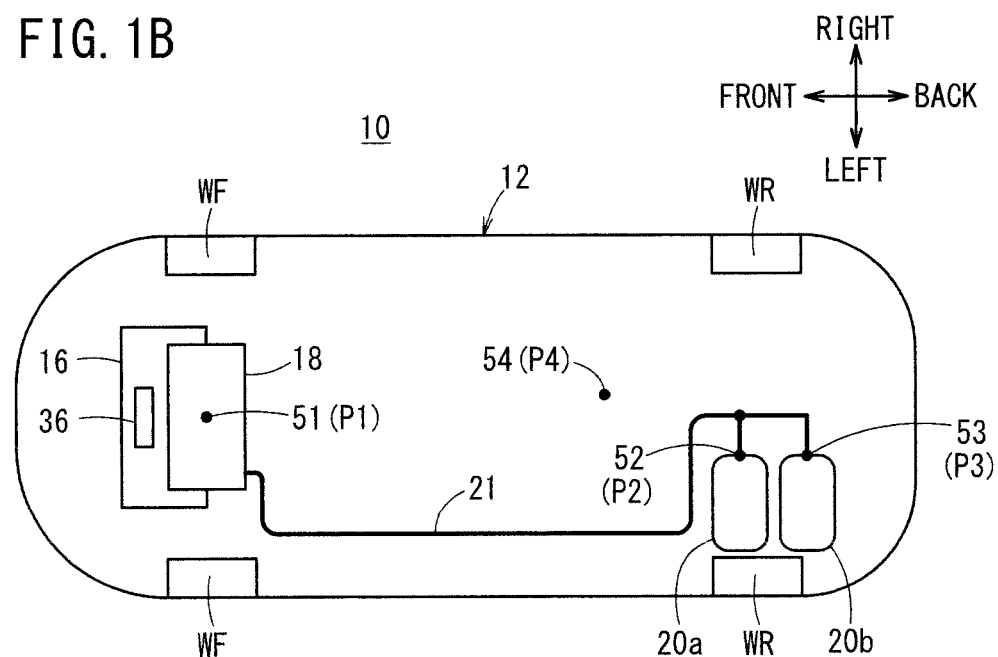
FIG. 1B is a plan view schematically showing the structure of the fuel cell vehicle.
Figure 2:
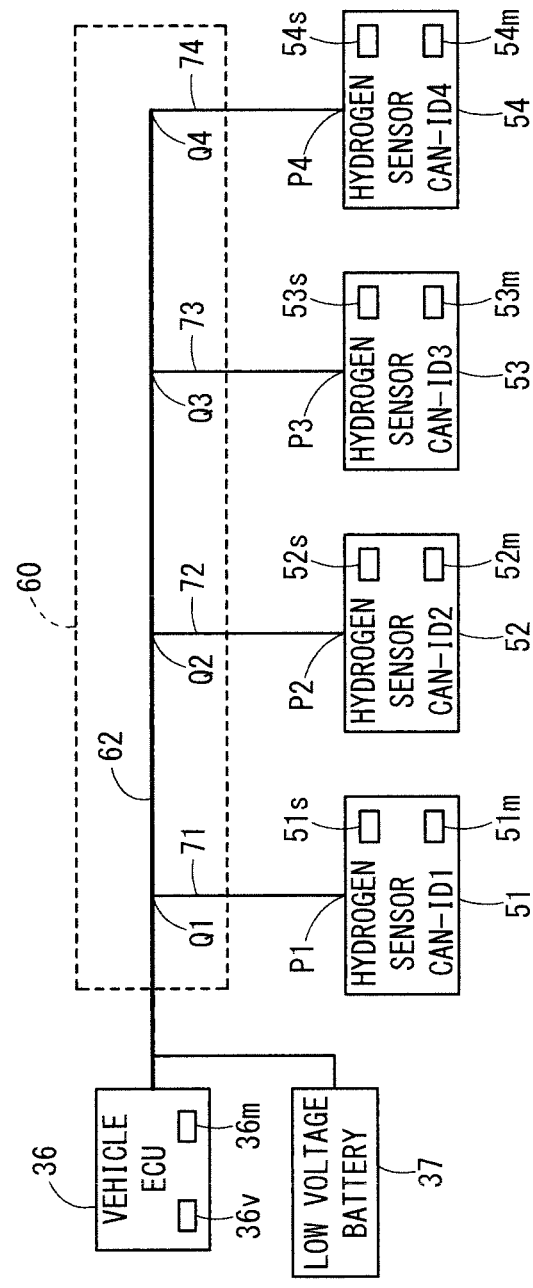
FIG. 2 is a circuit block diagram showing the gas monitoring system.

FIG. 1A is a side view schematically showing the structure of a fuel cell vehicle 12, which is equipped with a gas monitoring system for carrying out a gas monitoring method according to the present embodiment. FIG. 1B is a plan view schematically showing the structure of the fuel cell vehicle 12. FIG. 2 is a circuit block diagram showing the gas monitoring system 10.

As shown in FIGS. 1A and 1B, the fuel cell vehicle 12 includes a base frame 14. Components such as front wheels WF, rear wheels WR, a traction motor 16 for driving the front wheels WF, a fuel cell stack 18, hydrogen tanks 20a, 20b, a pipe 21, and a battery 19 (high voltage battery) are supported directly, or through structural bodies, on the base frame 14. In the following description, a front-back direction, a left-right direction, and an upper-lower direction are in accordance with the front, rear, left, right, upper, and lower arrows shown in FIGS. 1A and 1B.

Since the fuel cell vehicle 12 is of a known structure, only a brief description of the fuel cell vehicle 12 will be provided. The fuel cell vehicle 12 includes a fuel cell system. The fuel cell system includes a fuel cell stack 18 having a membrane electrode assembly (MEA) including a cathode, an anode, and a solid polymer electrolyte membrane, which is interposed between the cathode and the anode. The solid polymer electrolyte membrane is formed by impregnating a thin membrane of perfluorosulfonic acid with water, for example. Further, the fuel cell system includes hydrogen tanks 20a, 20b for supplying hydrogen as one reactant gas to the fuel cell stack 18, and an air pump (not shown) for supplying an oxygen-containing gas (air) as another reactant gas to the fuel cell stack 18. In addition, the fuel cell vehicle 12 includes a battery 19 for storing electrical energy generated by electrochemical reactions that take place in the fuel cell stack 18, and a traction motor 16, which serves as a drive source driven by electrical energy from the battery 19 for enabling the fuel cell vehicle 12 to be driven (i.e., placed in a traveling state).

The fuel cell vehicle 12 includes a front hood 22, a front window 24, a roof 26, a rear gate 28, a floor plate 30, a luggage room plate 32, a dash panel 34, a front seat 42, and a rear seat 44, etc. A display device 35 such as a multi-informational display is attached to the dash board at a location above the dash panel 34.

Further, a vehicle ECU (vehicle control ECU) 36 for controlling the gas monitoring system 10 of the fuel cell vehicle 12 as well as controlling the fuel cell vehicle 12, the fuel cell stack 18, and the traction motor as a whole, is positioned in a front engine room 38 underneath the front hood 22.

The battery 19 is provided under the rear seat 44, between a luggage room plate 32 and the base frame 14. The hydrogen tanks 20a, 20b are arranged in the front-back direction under a luggage room 46, between the luggage room plate 32 and the base frame 14. The hydrogen tanks 20a, 20b and the fuel cell stack 18 are interconnected by a pipe (hydrogen channel) 21 (see FIG. 1A) that passes underneath the floor plate 30.

Further, hydrogen sensors 51 to 54, which serve as gas sensors, are attached at four positions in the fuel cell vehicle 12. First, a hydrogen sensor 51 is attached at a position P1 underneath the front hood 22 and above the fuel cell stack 18. The fuel cell stack 18 serves as a target of gas leakage detection (leakage detection target). Secondly and thirdly, hydrogen sensors 52, 53 are attached at positions P2, P3 underneath the luggage room plate 32, and which are arranged above positions adjacent to interruption valves of the hydrogen tanks 20a, 20b. The hydrogen tanks 20a, 20b serve as targets of gas leakage detection, respectively, by the hydrogen sensors 52 and 53. Fourth, a hydrogen sensor 54 is attached at a position P4 underneath a central region of a roof 26 of a vehicle compartment 55. The pipe 21, which extends underneath the floor plate 30, is a main target of gas leakage detection (leakage detection target) by the hydrogen sensor 54.

Since hydrogen gas is lighter than air, if gas leakage occurs in any of the fuel cell stack 18, the pipe 21, and the hydrogen tanks 20a, 20b, which serve as gas leakage detection targets, the gas is retained in a recess above a position at which such leakage occurs. Therefore, the hydrogen sensors 51, 52, 53, 54 are attached at the positions P1, P2, P3, P4 where substantially downwardly-oriented recesses are formed. Preferably, the downwardly-oriented recesses are provided and serve as hydrogen pools at the positions P1, P2, P3, P4. In addition, the hydrogen sensors 51 to 54 are attached at respective peaks of the downwardly-oriented recesses.

Each of the vehicle ECU 36 and the hydrogen sensors 51 to 54 has a calculator including a microcomputer. The microcomputer includes a CPU (central processing unit), a ROM that serves as a memory (the memory may include an EEPROM), and a RAM (random access memory). Additionally, the microcomputer includes input/output devices such as an A/D converter, a D/A converter, and a timer, which serves as a time counter unit. The CPU reads a program that is recorded in the ROM, and executes the program in order to function as respective units, e.g., as a control unit, a computation unit, and a processing unit, for realizing various functions (function realizing means).

In the present embodiment, as shown in FIG. 2, the vehicle ECU 36 has an ID checking unit 36v, etc., as a functional unit, and the hydrogen sensors 51 to 54 have ID setting units 51s, 52s, 53s, 54s as respective functional units thereof.

The vehicle ECU 36 and the hydrogen sensors 51 to 54 have rewritable memory units 36m and 51m, 52m, 53m, 54m, respectively. Preferably, the rewritable memory units 36m and 51m, 52m, 53m, 54m are non-volatile memories. However, if necessary, volatile memories may also be used as the rewritable memory units 36m and 51m, 52m, 53m, 54m.

The vehicle ECU 36 and the hydrogen sensors 51 to 54 are interconnected by the vehicle harness 60.

Figure 3:
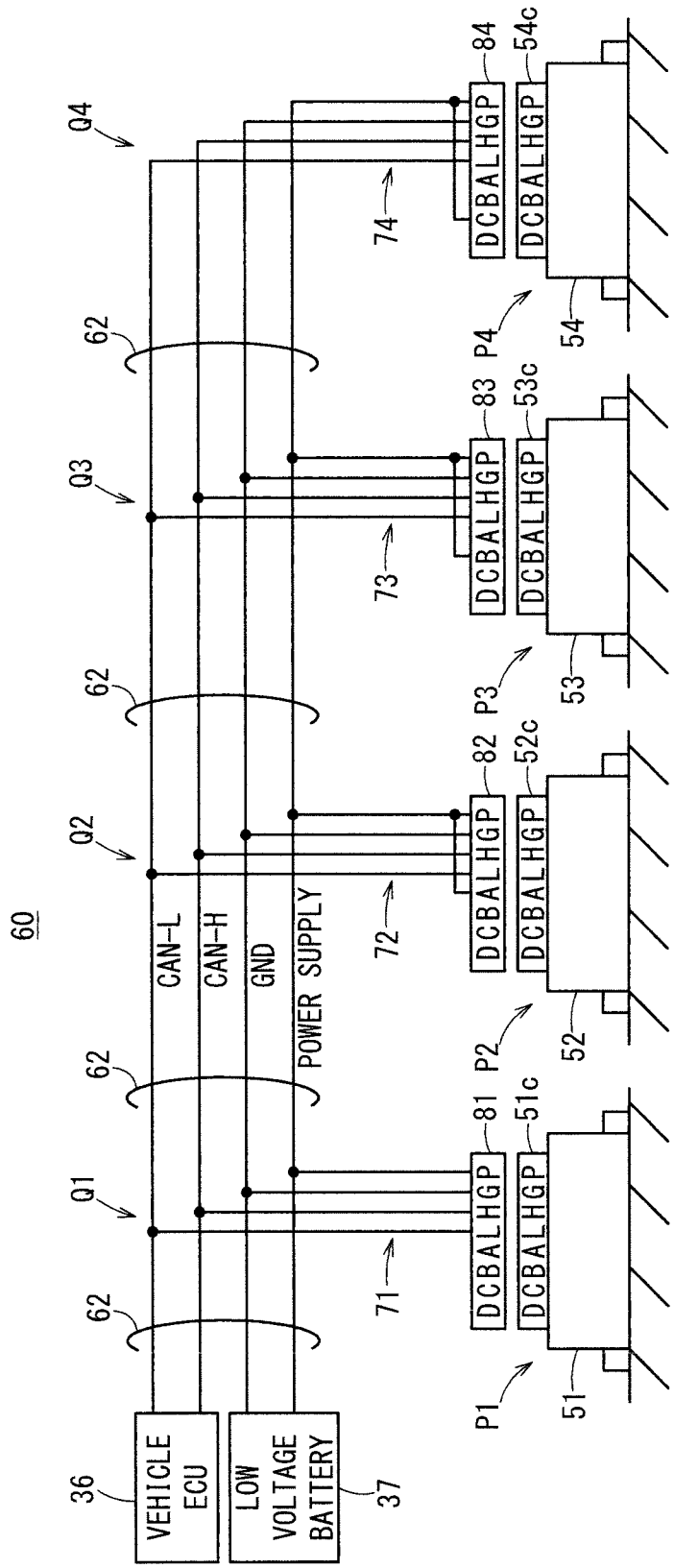
FIG. 3 is an actual wiring diagram schematically showing a vehicle harness, which includes a trunk line and branch line assemblies, a vehicle ECU, and hydrogen sensors.

As shown in FIG. 3, the vehicle harness 60 includes a trunk line 62, which serves as a CAN bus (communication bus), and four branch line assemblies 71, 72, 73, 74 that extend respectively from positions Q1, Q2, Q3, Q4 on the trunk line 62 (at the time that the trunk line 62 is wired in the fuel cell vehicle 12, the positions Q1, Q2, Q3, Q4 are provided substantially on the trunk line in alignment with the positions P1, P2, P3, P4 on the fuel cell vehicle 12.

The trunk line 62 is not limited to a CAN bus. Alternatively, other communication buses, such as a LIN bus or a FlexRay bus, may be used.

FIG. 3 is an actual wiring diagram schematically showing the vehicle harness 60, which includes the trunk line 62 and the branch line assemblies 71 to 74, the vehicle ECU 36, a low voltage battery 37, and the hydrogen sensors 51 to 54.

The trunk line 62 comprises a power supply line and a GND line, which extend from the low voltage battery (not shown in FIGS. 1A and 1B) provided in the front engine room 38, and a CAN-H line and a CAN-L line, which extend from the vehicle ECU 36. Branch line assemblies 71 to 74, each of which comprises a connector with a lead, are attached to the positions Q1 to Q4.

When the trunk line 62 is wired in the fuel cell vehicle 12, the low voltage battery 37 and the vehicle ECU 36 serve as a start terminal (starting point) of the trunk line 62. From the position of the vehicle ECU 36, first, the trunk line 62 is wired to the attachment position P1 of the hydrogen sensor 51, whereas the branch line assembly 71 is provided at the position Q1. Next, the trunk line 62 is laid underneath the floor plate 30, and is wired to the attachment positions P2, P3 of the hydrogen sensors 52, 53. The branch line assemblies 72, 73 are provided at the positions Q2, Q3. Next, the trunk line 62 is wired so as to pass inside of a C pillar (not shown) and through the roof 26. The attachment point P4 of the hydrogen sensor 54 serves as an end terminal (end point). The branch line assembly 74 is provided at the position Q4. In the layout (wiring configuration), non-illustrated terminal resistors for suppressing reflection of transmission signals (CAN data signals) are attached to an input/output terminal of the vehicle ECU 36, which is provided at the start terminal (starting point) of the trunk line 62 (transmission line), and an input/output terminal of the hydrogen sensor 54 is provided at the end terminal (end point) of the trunk line (transmission line), respectively.

The branch line assemblies 71 to 74 are attached to the trunk line 62 at the positions Q1 to Q4, and female type 8-pole connectors 81 to 84 are attached to ends of the branch line assemblies 71 to 74 for connection to the hydrogen sensors 51 to 54. The hydrogen sensors 51 to 54, which are provided at the positions P1 to P4 in facing relation to the positions Q1 to Q4, have male type 8-pole connectors 51c to 54c, and the connectors 81 to 84 are detachably connectable to the male type 8-pole connectors 51c to 54c.

Each of the 8-pole connectors 81 to 84 of the branch line assemblies 71 to 74 includes female pins indicated by power supply-P, GND-G, CAN-H, CAN-L, identification A, identification B, identification C, and identification D. Likewise, each of the 8-pole connectors 51c to 54c of the hydrogen sensors 51 to 54 includes male pins indicated by power supply-P, GND-G, CAN-H, CAN-L, identification A, identification B, identification C, and identification D, in corresponding relation to the female pins, respectively. The connectors 81 to 84 of the trunk line 62 and the connectors 51c to 54c of the hydrogen sensors 51 to 54 are configured such that the connectors 81 to 84 and 51c to 54c cannot be fitted together in a wrong or opposite orientation.

Next, identification configurations, which are unique to each of the respective connectors 81 to 84, will be described. The connector 81 has an identification configuration (referred to as identification configuration 1) in which an inter-pole short circuiting wire (described later) is not provided between any pairs of the female pins. The connector 82 has an identification configuration 2 in which the power supply-P pin and the identification A pin are short circuited by a jumper wire, etc., which serves as an inter-pin short circuiting wire. The connector 83 has an identification configuration 3 in which the power supply-P pin and the identification B pin are short-circuited by a jumper wire, etc. The connector 84 has an identification configuration 4 in which the power supply-P pin and the identification C pin are short-circuited by a jumper wire, etc. That is, the branch line assemblies 71 to 74 are different only in respect to the position where the jumper wire is inserted in the connectors 81 to 84. In this manner, the branch line assemblies 71 to 74 have respective identification configurations 1 to 4, whereby the branch line assemblies 1 to 4 can be uniquely identified electrically.

Therefore, when the power supply of the gas monitoring system 10 is turned on, the hydrogen sensors 51 to 54 (the CPUs of the hydrogen sensors 51 to 54) determine the identification configurations 1 to 4 of the connectors 81 to 84 (branch line assemblies 71 to 74) that are fitted to the connectors 51c to 54c. Accordingly, it is possible to identify (distinguish) a correspondence between the connectors 81 to 84, which are fitted to the connectors 51c to 54c, and the branch line assemblies 71 to 74.

In an effort to reduce the number of production steps for the vehicle harness 60, the branch line assemblies 71 to 74 have the same lead length. Conversely, the branch line assemblies 71 to 74 may have different lead lengths, so as to permit the branch line assemblies 71 to 74 to be identified based on the lengths of the branch line assemblies 71 to 74.

Figure 4:
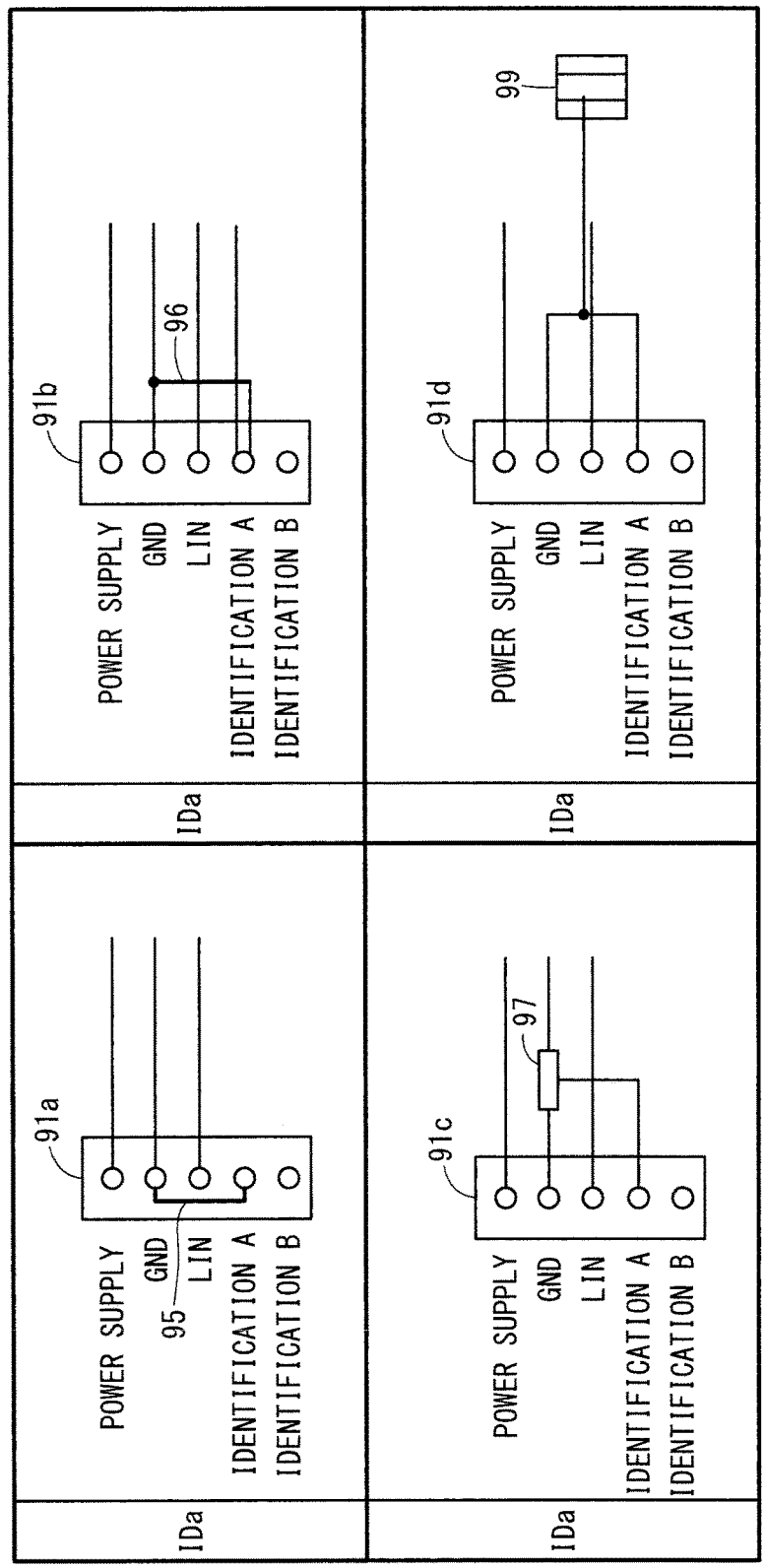
FIG. 4 is a diagram illustrating connections by 5-pole connectors, each having the same identification configuration, adopted in a LIN bus.
Figure 5:
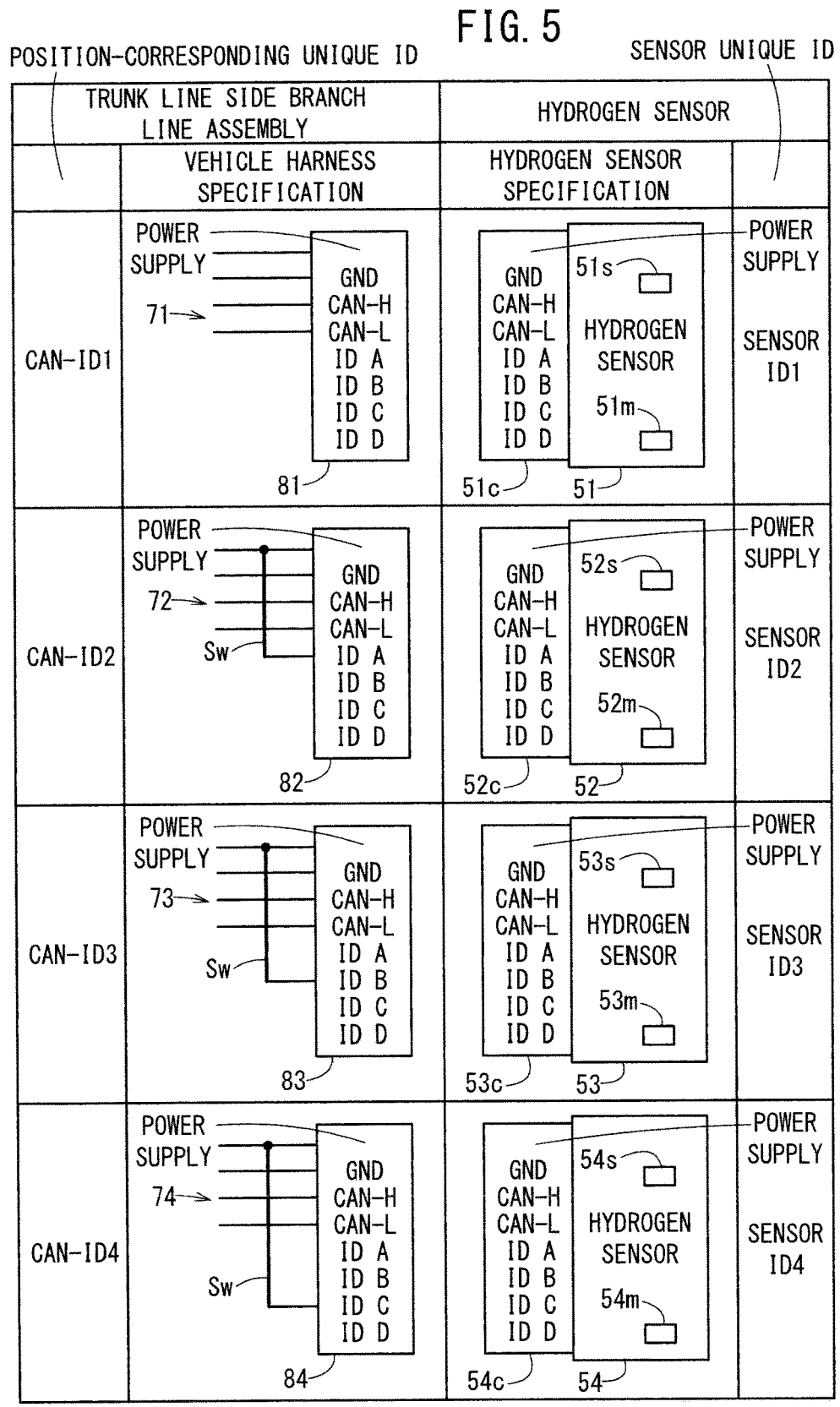
FIG. 5 is a connection configuration diagram of a branch line assembly having fifteen different IDs, which are assignable by changing pin positions (pole positions) at respective opposite ends of a short circuiting wire provided between the pins (between poles) of an 8-pole connector.
Figure 7:
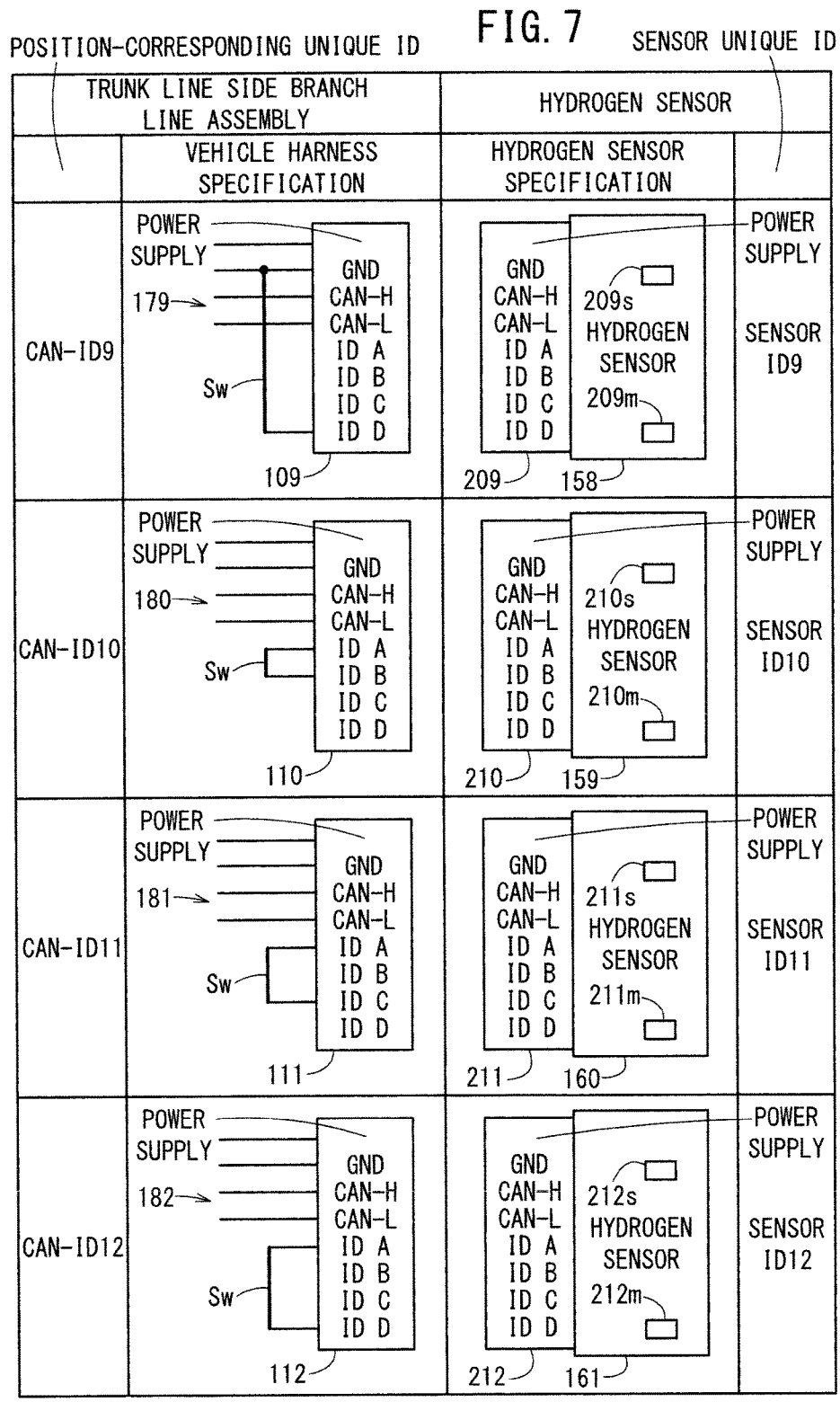
FIG. 7 is still another connection configuration diagram of the branch line assembly having fifteen different IDs, which are assignable by changing pin positions (pole positions) at respective opposite ends of a short circuiting wire provided between the pins (between poles) of an 8-pole connector.
Figure 8:
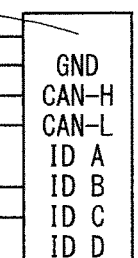
FIG. 8 is still another connection configuration diagram of the branch line assembly having fifteen different IDs, which are assignable by changing pin positions (pole positions) at respective opposite ends of a short circuiting wire provided between the pins (between poles) of an 8-pole connector.

FIG. 4 shows examples of wire connections for an identification IDa having the same identification configuration, in the 5-pole connectors 91a to 91d that are incorporated in the LIN bus. For example, as shown in the upper left portion of FIG. 4, the GND pin and the identification A pin are connected by a connector internal bus bar 95. As shown in the upper right portion of FIG. 4, the wire from the GND pin and the wire from the identification A pin are connected by a connector external jumper 96. As shown in the lower left portion of FIG. 4, the wire from the GND pin branches from a connector external joint terminal 97, and is connected to the wire from the identification A pin. As shown in the lower right portion of FIG. 4, the wire from the GND pin branches from a connecter external joint connector 99, and is connected to the wire from the identification A pin. In this manner, different forms of wire connections (short circuiting wire connections between poles) may be adopted in the identification IDa having the same identification configuration.

As can be understood from FIGS. 3 and 4, as for the number of poles of the connector of the branch line assembly, as a minimum configuration for identifying gas sensors (e.g., hydrogen sensors) having the same specification and which are connected to the connector, it is necessary to provide a number of poles for at least one identification pin in addition to the pins provided for the bus line (four pins (P, G, H, L) in the example of FIG. 3, and three pins (power supply, GND, LIN) in the example of FIG. 4).

FIGS. 5 to 8 show examples of configurations when branch line assemblies 71 to 74 and 175 to 185 having 15 different IDs are configured by changing pin positions (pole positions) at respective ends of an inter-pin short circuiting wire (inter-pole short circuiting wire) of 8-pole connectors (the above-described connectors 81 to 84, etc.). Note that in FIGS. 5 to 8, hydrogen sensors 51 to 54 and 154 to 164 also are shown, having connectors 51c to 54c and 205 to 215, setting units 51s to 54s and 205s to 215s, and memory units 51m to 54m and 205m to 215m.

In the fifteen branch line assemblies 71 to 74 and 175 to 185, among the position-corresponding unique IDs (CAN-ID1 to CAN-ID15) of the trunk line 62, male pins of identifications A to C, which are assigned to the position-corresponding unique ID (CAN-ID1), are not connected to any of the male pins of the power supply (having the same meaning as the above-described power supply-P), GND (having the same meaning as the above described GND-G), CAN-H, and CAN-L (CAN-ID1: referred to as a nonconnection). This configuration is referred to as identification configuration 1. Hereinafter, in the following list, in addition to identification configuration 1 having the position-corresponding unique ID CAN-ID1, identification configurations 2 to 15 for the other position-corresponding unique IDs will be explained.

Identification configuration 1 (CAN-ID1): None of the power supply, GND, CAN-H, and CAN-L, and identifications A to D are connected.

Identification configuration 2 (CAN-ID2): The power supply and identification A are connected by a short circuiting wire Sw.

Identification configuration 3 (CAN-ID3): The power supply and identification B are connected by the short circuiting wire Sw.

Identification configuration 4 (CAN-ID4): The power supply and identification C are connected by the short circuiting wire Sw.

Identification configuration 5 (CAN-ID5): The power supply and identification D are connected by the short circuiting wire Sw.

Identification configuration 6 (CAN-ID6): GND and identification A are connected by the short circuiting wire Sw.

Identification configuration 7 (CAN-ID7): GND and identification B are connected by a short circuiting wire Sw.

Identification configuration 8 (CAN-ID8): GND and identification C are connected by the short circuiting wire Sw.

Identification configuration 9 (CAN-ID9): GND and identification D are connected by the short circuiting wire Sw.

Identification configuration 10 (CAN-ID10): Identification A and identification B are connected by the short circuiting wire Sw.

Identification configuration 11 (CAN-ID11): Identification A and identification C are connected by the short circuiting wire Sw.

Identification configuration 12 (CAN-ID12): Identification A and identification D are connected by the short circuiting wire Sw.

Identification configuration 13 (CAN-ID13): Identification B and identification C are connected by the short circuiting wire Sw.

Identification configuration 14 (CAN-ID14): Identification B and identification D are connected by the short circuiting wire Sw.

Identification configuration 15 (CAN-ID15): Identification C and identification D are connected by the short circuiting wire Sw.

It should be noted that the hydrogen sensors 51 to 54 and the hydrogen sensors 154 to 164, of which there are fifteen in total, are the same, i.e., have the same specification before the sensor IDs (sensor ID1 to sensor ID15), which serve as sensor unique IDs corresponding to the identification configuration 1 (CAN-ID1) to the identification configuration 15 (CAN-ID15) and are associated with information concerning the positions P1 to P15 (or the positions Q1 to Q15), are written into the memory units 51m to 54m and the memory units 205m to 215m of the fifteen hydrogen sensors 51 to 54 and 154 to 164. Stated otherwise, the fifteen hydrogen sensors 51 to 54 and 154 to 164 have a single specification (i.e., the same specification), and are suitable for mass production. Consequently, it is possible to reduce production costs as well as component management costs.

FIG. 9 is a diagram showing a configuration of branch line assemblies 301 to 304 (connectors 311 to 314 and three lead wires, i.e., a power supply wire, a GND wire, and a LIN wire) having four different position-corresponding unique IDs created by changing pin positions (pole positions) at respective opposite ends of a short circuiting wire provided between the pins (between poles) of a 5-pole connector that is incorporated in a LIN bus.

In the branch line assembly 301, in correspondence with the position-corresponding unique IDs (LIN-ID1 to LIN-ID4) of the trunk line, for example, the male pin of GND of the position-corresponding unique ID LIN-ID1 is connected to the male pin of identification A. Such a configuration is referred to as an identification configuration 1a. Hereinafter, in the same manner, in addition to the identification configuration 1a, other identification configurations will be explained in the following list.

Identification configuration 1a (LIN-ID1): GND and identification A are connected by a short circuiting wire Sw.

Identification configuration 2a (LIN-ID2): GND and identification B are connected by a short circuiting wire Sw.

Identification configuration 3a (LIN-ID3): Identification A and identification B are connected by a short circuiting wire Sw.

Identification configuration 4a (LIN-ID4): None of the pins are connected.

Also in this case, before the connectors 401 to 404 of the hydrogen sensors 221 to 224 are connected respectively to the trunk line connectors 311 to 314, and the sensor IDs (sensor ID1 to sensor ID4), which serve as sensor unique IDs, are written into the memory units 221m to 224m, all of the hydrogen sensors 221 to 224 are the same. Stated otherwise, the hydrogen sensors 221 to 224 have a single specification (i.e., the same specification), and are suitable for mass production. Consequently, it is possible to reduce production costs as well as component management costs.

Next, the gas monitoring method according to the present embodiment will be described below with reference to an example of an assembly process and an inspection process, which are performed when the hydrogen sensors 51 to 54 are attached to a fuel cell vehicle 12 to which the gas monitoring method is applied.

Figure 10:
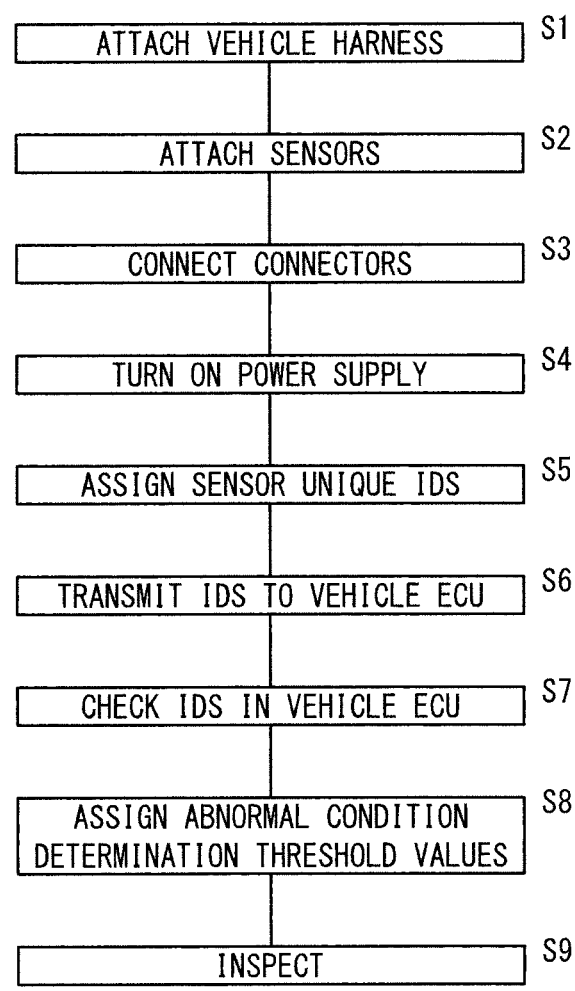
FIG. 10 is a flow chart schematically showing a series of processes, ranging from a vehicle harness attachment process to a completion line inspecting process, for the gas monitoring system, which takes place during a production process for a fuel cell vehicle.

FIG. 10 is a flow chart schematically showing a series of processes, ranging from a vehicle harness attachment process to a gas completion line inspecting process, for the gas monitoring system 10, which takes place during a production process for the fuel cell vehicle 12.

In practice, before the vehicle harness attachment process of step S1, among the components shown in FIGS. 1A and 1B, it is assumed that necessary parts other than the vehicle harness 60 (trunk line 62 having the branch line assemblies 71 to 74 attached thereto) and the hydrogen sensors 51 to 54 shown in FIG. 3, for example, the vehicle ECU 36, etc., have already been assembled in the fuel cell vehicle 12.

In the vehicle harness attachment process of step S1, in a state in which the power supply of the fuel cell vehicle 12 is turned off, the start terminal of the vehicle harness 60 is attached to the vehicle ECU 36, whereas the remainder of the vehicle harness 60 is provided along a predetermined position on the fuel cell vehicle 12. In the present embodiment, as described above, the branch line assembly 71, which is disposed at the position Q1 on the trunk line 62 of the vehicle harness 60, is arranged in confronting relation to the position P1. Then, the vehicle harness 60 is laid out backward and downward from the front engine room 38, and is further laid out under the floor plate 30. In addition, the vehicle harness 60 is wired such that the branch line assemblies 72, 73, which are disposed at the positions Q2, Q3 of the trunk line 62, are arranged in confronting relation to the positions P2, P3. Further, the vehicle harness is wired so as to pass inside of the C pillar and through the roof 26, such that the branch line assembly 74 at the terminal end position Q4 of the trunk line 62 is arranged in confronting relation to the position P4, thereby completing the wiring operation of the trunk line 62 of the vehicle harness 60.

Next, in the sensor attachment process of step S2, hydrogen sensors 51 to 54 having the same specification (a single specification, of the same type) are attached to positions P1 to P4 in the fuel cell vehicle 12. In this case, since the hydrogen sensors 51 to 54 have the same specification, and can be attached to any of the positions P1 to P4, so called erroneous assembly does not occur. It should be noted that attachment of the hydrogen sensors 51 to 54 may be performed prior to attachment of the vehicle harness 60.

Next, in the connector connection process of step S3, the connectors 51c to 54c of the hydrogen sensors 51 to 54 are fixed at the positions P1 to P4. In addition, the connectors 81 to 84 of the branch line assemblies 71 to 74, which have already been disposed in positions adjacent to the connectors 51c to 54c, are fitted to the connectors 51c to 54c. In this manner, the male pins of the connectors 51c to 54c of the hydrogen sensors 51 to 54 are connected mechanically and electrically to the female pins of the connectors 81 to 84.

Further, in a process of turning on the power supply, in step S4, the power supply of the fuel cell vehicle 12 is placed in an ON state. Thus, electrical energy is supplied from the low voltage battery 37 to the vehicle ECU 36. In addition, electrical energy is supplied from the low voltage battery 37, through the power supply line and the GND line of the trunk line 62, to the hydrogen sensors 51 to 54.

Supply of electrical energy triggers the CPUs of the hydrogen sensors 51 to 54 in order to start an initial setup operation including the sensor unique ID setting process of step S5.

In step S5, the ID setting units 51s to 54s of the hydrogen sensors 51 to 54 recognize the identification configurations 1 to 4 (which pins are short circuited) of the position-corresponding unique IDs (CAN-ID1 to CAN-ID4), which are assigned to the connectors 81 to 84 of the branch line assembly 71 to 74 by the jumper wire. Further, the ID setting units 51s to 54s write the recognition results in the memory units 51m to 54m, so as to store the data as sensor IDs (sensor ID1 to sensor ID4), which serve as unique IDs for the hydrogen sensors 51 to 54 associated with information concerning the positions P1 to P4 of the hydrogen sensors 51 to 54 (or the positions Q1 to Q4 of the branch line assemblies 71 to 74) (ID setting process).

More specifically, in the present embodiment, the ID setting units 51s to 54s write the sensor IDs (sensor ID1 to sensor ID4), which correspond respectively to the position-corresponding unique IDs (i.e., identification configuration 1 (CAN-ID1): none of the power supply and identifications A to D are connected, identification configuration 2 (CAN-ID2): the power supply and identification A are connected, identification configuration 3 (CAN-ID3) the power supply and identification B are connected, and identification configuration 4 (CAN-ID4): the power supply and identification C are connected), in the memory units 51m to 54m.

Next, during the process of transmitting IDs to the vehicle ECU 36, in step S6, the ID setting units 51s to 54s of the hydrogen sensors 51 to 54 read the sensor IDs (sensor ID1 to sensor ID4) corresponding to the identification configurations 1 to 4 (CAN-ID1 to CAN-ID4) as unique IDs that are written in the memory units 51m to 54m. In addition, the ID setting units 51s to 54s transmit the sensor IDs (sensor ID1 to sensor ID4) to the vehicle ECU 36 by way of serial communications through the trunk line 62 (unique ID transmission process).

Next, in the ID checking process, which is performed in the vehicle ECU 36 in step S7, an ID checking unit 36v of the vehicle ECU 36 checks the sensor IDs (sensor ID1 to sensor ID4), as unique IDs assigned to the hydrogen sensors 51 to 54 and which are received by the vehicle ECU 36, for matching with the identification configurations 1 to 15 (CAN-ID1 to CAN-ID15), as position-corresponding unique IDs that are stored by the vehicle ECU in correspondence with information concerning the positions Q1 to Q4 of the trunk line 62. Based on the checking result, it is possible to identify (distinguish) the sensor IDs (sensor ID1 to sensor ID4) as unique IDs of the hydrogen sensors 51 to 54, which are attached to the positions P1 to P4 corresponding to the identification configurations 1 to 4 (CAN-ID1 to CAN-ID4) as position-corresponding unique IDs.

Further, in the setting process for the abnormal condition determination threshold value, in the final step S8 of the initial setup, for each of the hydrogen sensors 51 to 54 identified by the sensor IDs (sensor ID1 to sensor ID4), via the ID setting units 51s to 54s, the vehicle ECU makes settings for abnormal condition determination thresholds Th, which are stored beforehand in a memory unit 36m, in correspondence with the positions P1 to P4 of the hydrogen sensors 51 to 54, and the positions of the fuel cell stack 18, the pipe 21, and the hydrogen tanks 20a, 20b, which serve as gas leakage detection targets. The vehicle ECU 36 stores the abnormal condition determination thresholds Th respectively in each of the memory units 51m to 54m.

Figure 11:
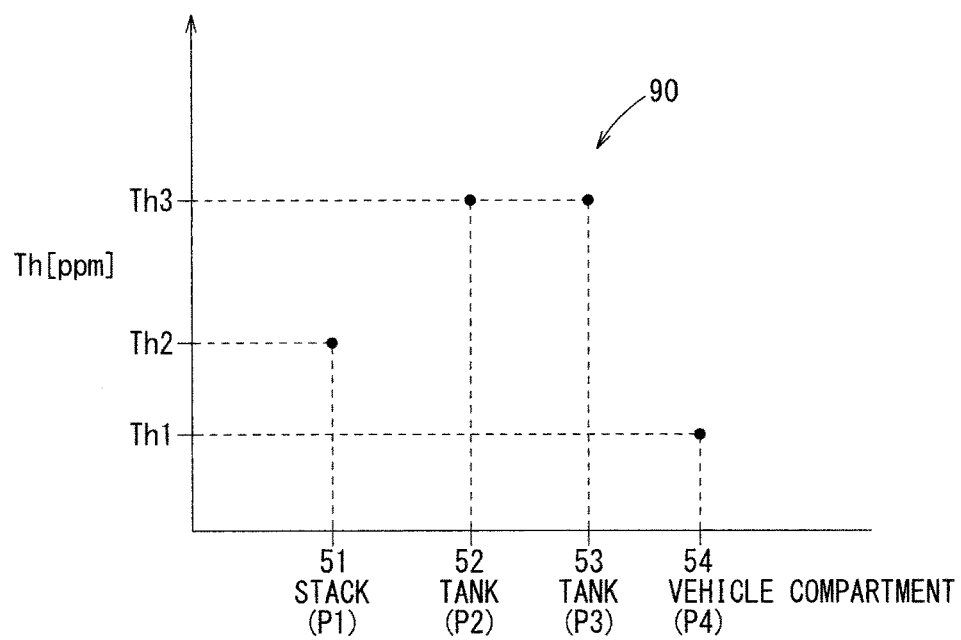
FIG. 11 is a graph showing abnormal condition determination threshold values, which are stored in a memory of a vehicle ECU.

FIG. 11 is an abnormal condition determination threshold table 90, which is stored beforehand in the memory unit 36m.

The abnormal condition determination threshold value Th becomes lower as the distance between the hydrogen sensors 51 to 54 and the gas leakage detection target closest to the hydrogen sensors 51 to 54 becomes large. Therefore, the abnormal condition determination threshold Th of the hydrogen sensor 54, which is placed under the central position of the roof 26 of the vehicle compartment 55 remotely from the pipe 21 under the floor plate 30, is stored in the memory unit 54m as a lowest abnormal condition determination threshold value Th1. Then, an abnormal condition determination threshold value Th2 of the second remotest hydrogen sensor 51, which is placed below the front hood 22 and above the fuel cell stack 18, is stored in the memory unit 51m. An abnormal condition determination threshold value Th3 is stored in the memory units 52m, 53m of the hydrogen sensors 52, 53, which are placed at closest positions immediately above the hydrogen tanks 20a, 20b. More specifically, the same abnormal condition determination threshold value Th3 is stored in both of the memory units 52m, 53m.

Figure 12:
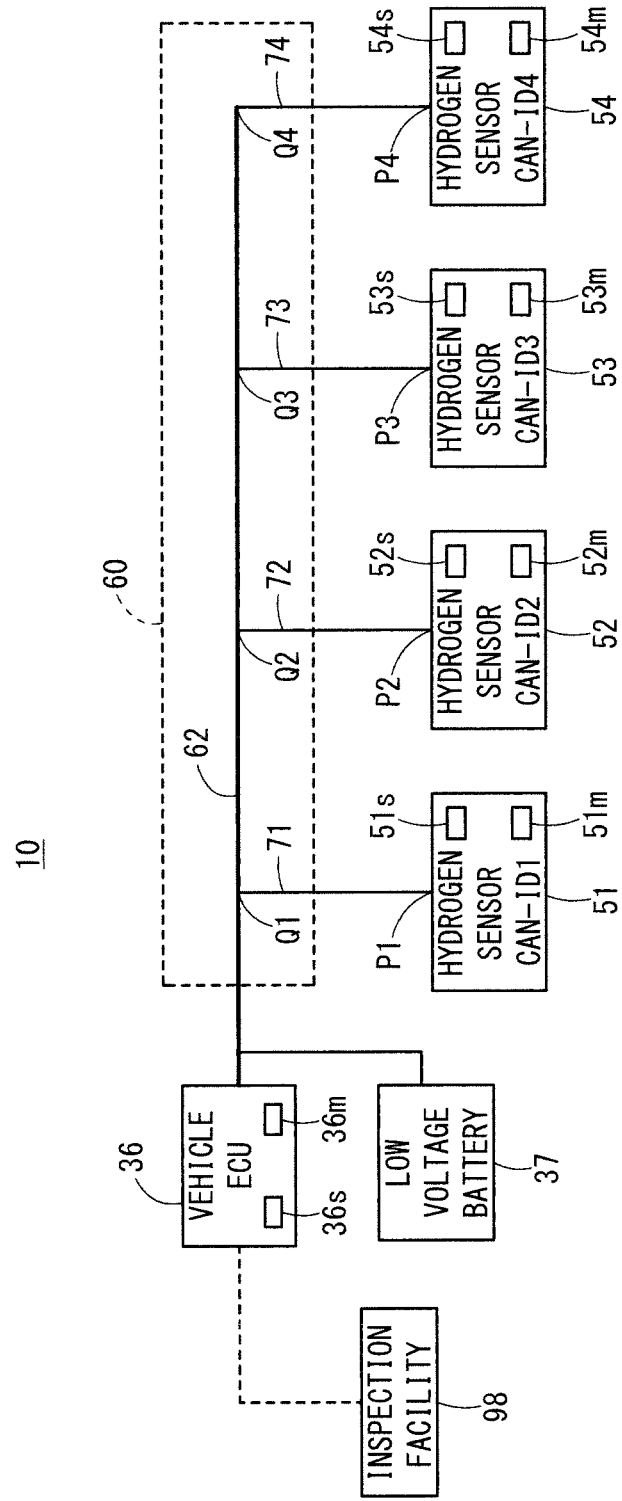
FIG. 12 is a circuit block diagram showing the gas monitoring system in a condition of being connected to an inspection facility.

Next, following completion of the initial setup, in the completion line inspection process of the gas monitoring system performed in step S9, as shown in FIG. 12, an inspection facility 98 is connected to the vehicle control ECU 36. The inspection facility 98 confirms matching of the identification IDs, initial characteristics (zero value settings) of the hydrogen sensors 51 to 54, and self-diagnosis results of the hydrogen sensors 51 to 54, in order to finish a series of processes, ranging from the vehicle harness attachment process to the completion line inspection process, for the gas monitoring system 10 that is mounted in the fuel cell vehicle 12.

Thereafter, after the inspection facility 98 has been removed and the power supply of the fuel cell vehicle 12 as a completed vehicle has been turned on, the hydrogen sensors 51 to 54 detect the hydrogen concentration continuously (i.e., at all times) at positions where the hydrogen sensors 51 to 54 are attached. Further, the log data is stored for a predetermined time in the memory units 51m to 54m. When the hydrogen concentration exceeds the abnormal condition determination threshold values Th, the hydrogen sensors 51 to 54 transmit the log values and the abnormal values (both detected values) together with their own unique IDs, i.e., the sensor IDs (sensor ID1 to sensor ID4), to the vehicle ECU 36 (detection value transmitting step). At this time, the vehicle ECU 36 generates an alarm signal in order to display an alarm on the display device 35, thereby providing a notification that the hydrogen concentration of the leaked hydrogen has exceeded the abnormal condition determination threshold values Th. Further, the positions P1 to P4 of the hydrogen sensors 51 to 54, for which abnormal values have been detected, may be identified and displayed.

SUMMARY OF THE EMBODIMENT

As described above, the gas monitoring system 10 according to the present embodiment is mounted in the fuel cell vehicle 12, and uses the hydrogen sensors 51 to 54 that are connected to one trunk line 62. The gas monitoring system 10 includes the hydrogen sensors 51 to 54 that are provided at the predetermined positions P1 to P4. The hydrogen sensors 51 to 54 include the connectors 51c to 54c, and a plurality of unique IDs can be assigned to the hydrogen sensors 51 to 54. Further, the gas monitoring system 10 includes the connectors (trunk line connectors) 81 to 84, which are provided for the trunk line 62, and the connectors 51c to 54c of the hydrogen sensors 51 to 54 are fittable to the trunk line connectors 81 to 84. Moreover, the gas monitoring system 10 includes the vehicle ECU 36, which serves as a control device connected to the trunk line 62, for thereby controlling the hydrogen sensors 51 to 54.

The connectors 81 to 84, which are attached to the branch line assemblies 71 to 74 that extend from the trunk line 62, include the identification configurations 1 to 4 (CAN-ID1 to CAN-ID4) for allowing the position information concerning the connectors 81 to 84 of the trunk line 62 to be identified. The hydrogen sensors 51 to 54 include ID setting units 51s to 54s for assigning, based on the identification configurations 1 to 4 (CAN-ID1 to CAN-ID4) of the trunk line connectors 81 to 84, the sensor IDs (sensor ID1 to sensor ID4) as unique IDs to the hydrogen sensors 51 to 54, when the connectors 51c to 54c of the hydrogen sensors 51 to 54 are fitted to the trunk line connectors 81 to 84. The vehicle ECU 36 also includes the memory unit 36m, which functions as a gas sensor identification memory unit for storing information concerning the positions P1 to P4 of the hydrogen sensors 51 to 54 (or the positions Q1 to Q4 of the branch line assemblies 71 to 74) associated with the sensor IDs (sensor ID1 to sensor ID4) of the hydrogen sensors 51 to 54.

As described above, it is possible to identify the plural hydrogen sensors 51 to 54, which are connected to one trunk line 62 at the predetermined positions P1 to P4 (Q1 to Q4), in order to easily obtain information concerning the positions P1 to P4 of the hydrogen sensors 51 to 54. Further, since it is possible to use the hydrogen sensors 51 to 54 having a single specification (i.e., the same specification), management of parts or components can be performed easily. It is further possible to reduce component costs and component management costs. Moreover, erroneous assembly or assembly of mistaken components, etc., can be prevented.

In this case, the vehicle ECU 36 generates an alarm signal when a detection value of any of the hydrogen sensors 51 to 54 becomes equal to or greater than an abnormal condition determination threshold value Th1 to Th3, and different values are determined as abnormal condition determination threshold values Th1 to Th3 based on information concerning the positions P1 to P4 of the hydrogen sensors 51 to 54. Therefore, it is possible to generate a suitable alarm signal in correspondence with the positions P1 to P4 where the hydrogen sensors 51 to 54 are attached.

In this regard, the abnormal condition determination threshold values Th1 to Th3 are determined such that the abnormal condition determination threshold values Th1 to Th3 become lower (abnormal condition determination threshold value Th1 of the hydrogen sensor 54<abnormal condition determination threshold value Th2 of the hydrogen sensor 51<abnormal condition determination threshold value Th3 of the hydrogen sensors 52, 53) as the distance between the hydrogen sensor 51 to 54 and a target of leakage detection closest to the hydrogen sensor 51 to 54 becomes large (distance between the hydrogen sensor 51 and the fuel cell stack 18<distance between the hydrogen sensors 52, 53 and the hydrogen tanks 20a, 20b<distance between the hydrogen sensor 54 and the pipe 21). By providing the abnormal condition determination threshold values Th1 to Th3, which correspond with the attachment positions P1 to P4 of the hydrogen sensors 51 to 54, the abnormal condition determination can be performed precisely. Thus, it is possible to prevent detection of an abnormal condition in vain, and delays in detecting abnormal conditions can be avoided.

The gas monitoring method according to the present embodiment is a gas monitoring method that makes use of the hydrogen sensors 51 to 54 equipped with the connectors 51c to 54c having the single specification, and the connectors 51c to 54c of the hydrogen sensors 51 to 54 can be fitted to the connectors 51c to 54c of the trunk line 62. The connectors 81 to 84 of the trunk line 62 include the position-corresponding unique IDs, and are provided at plural positions Q1 to Q4 of the one trunk line 62 that is connected to the vehicle ECU 36.

When the connectors 51c to 54c of the hydrogen sensors 51 to 54 are fitted to the connectors 81 to 84 of the trunk line 62 along with the position-corresponding unique IDs, which serve as unique IDs in the ID setting process (step S5), the sensor IDs (sensor ID1 to sensor ID4), which correspond to the position-corresponding unique IDs of the connectors 81 to 84 of the trunk line 62, are assigned in the unique ID transmission process (step S6) as unique IDs to the hydrogen sensors 51 to 54, which are equipped with the connectors 51c to 54c fitted to the connectors 81 to 84. Further, the sensor IDs (sensor ID1 to sensor ID4), which are assigned to the hydrogen sensors 51 to 54 equipped with the connectors 51c to 54c, are transmitted to the vehicle ECU 36 through the trunk line 62. In the ID checking process (step S7), the sensor IDs (sensor ID1 to sensor ID4), which serve as unique IDs assigned to the hydrogen sensors 51 to 54 equipped with the connectors 51c to 54c and which are received by the vehicle ECU 36, are checked by the vehicle ECU 36 for matching with the position-corresponding unique IDs that correspond to the position information stored in correspondence with the positions Q1 to Q4 of the trunk line 62.

In the gas monitoring method according to the present embodiment, it is possible to identify the plural hydrogen sensors 51 to 54 that are connected to the one trunk line 62, in order to easily obtain information concerning the positions P1 to P4 of the hydrogen sensors 51 to 54. Since hydrogen sensors 51 to 54 having a single specification (i.e., the same specification) can be used, management of parts or components can be performed easily. Accordingly, it is possible to reduce component costs and component management costs. Moreover, erroneous assembly or assembly of mistaken components, etc., can be prevented.

Further, since the hydrogen sensors 51 to 54 are connected to the one trunk line 62 in a state in which information concerning the positions P1 to P4 can be identified, as shown in FIG. 12, inspection of the hydrogen sensors 51 to 54 at the time of completion of production can be performed in a short time period (at one time).

Further, the gas monitoring system 10 according to the present embodiment is mounted in the fuel cell vehicle 12, which is equipped with a fuel cell system, including components such as the fuel cell stack 18, the battery 19, etc. In addition, the gas monitoring method may be implemented in a fuel cell vehicle 12 that is equipped with such a fuel cell system including components such as the fuel cell stack 18, the battery 19, etc. In this case, the fuel cell vehicle 12 includes at least two hydrogen tanks 20a, 20b, and the hydrogen sensors 52, 53 are provided above the hydrogen tanks 20a, 20b, respectively. The vehicle ECU 36, i.e., the vehicle ECU 36 which implements the gas monitoring method, further includes a fuel supply continuation unit, in which, when any one of the hydrogen sensors 52, 53 provided above the hydrogen tanks 20a, 20b has detected an abnormal condition, the fuel supply continuation unit continues to supply hydrogen to the fuel cell stack 18 using only the hydrogen tank 20a or 20b that is provided below the hydrogen sensor 52 or 53 for which an abnormal condition has not been detected. In this manner, since by using the hydrogen tank 20a or 20b for which an abnormal condition has not been detected, it is possible to continue operation of the fuel cell system, an improvement in merchantability of the gas monitoring system can be achieved.

It is a matter of course that the present invention is not limited to the embodiment described above, and various alternative or additional structures can be adopted therein based on the descriptive content of the present specification.

What is claimed is:

1. A gas monitoring method using gas sensors equipped with connectors having a single specification, the connectors of the gas sensors being fittable to trunk line connectors with position-corresponding unique IDs provided at plural positions of one trunk line that is connected to a control device; the method comprising the steps of:

when the connectors of the gas sensors are fitted to the trunk line connectors along with the position-corresponding unique IDs, assigning unique IDs corresponding to the position-corresponding unique IDs of the trunk line connectors to the gas sensors, which are equipped with the connectors fitted to the trunk line connectors;

transmitting the unique IDs, which are assigned to the gas sensors equipped with the connectors, to the control device through the trunk line; and checking whether the unique IDs, which are assigned to the gas sensors equipped with the connectors and are received by the control device, match the position-corresponding unique IDs corresponding to the plural positions of the trunk line, wherein the position-corresponding unique IDs are stored at the control device, wherein the gas monitoring method is implemented in a fuel cell vehicle equipped with a fuel cell system, wherein the fuel cell vehicle includes at least two fuel tanks, wherein the gas sensors are provided above the fuel tanks, respectively, and wherein the control device further performs a fuel supply continuation step in which, when any one of the gas sensors provided above the fuel tanks has detected an abnormal condition, supply of fuel to a fuel cell is continued using only the fuel tank for which the gas sensor has not detected the abnormal condition.

2. The gas monitoring method according to claim 1, further comprising, in the step of checking the unique IDs, an abnormal condition determination threshold value setting step of storing, with respect to the gas sensors, abnormal condition determination threshold values in respective memory units of each of the gas sensors, for judging whether or not detection values of each of the gas sensors are abnormal, after the control device has checked that the unique IDs of the gas sensors match the position-corresponding unique IDs.

3. The gas monitoring method according to claim 2, in the case that the abnormal condition determination threshold values are set to different values based on the information concerning the positions where the respective gas sensors that serve as gas leakage detecting sensors are arranged, and any one of the detection values of the respective gas sensors is equal to or greater than the abnormal condition determination threshold values set based on the positions of the respective gas sensors, further comprising a detection value transmitting step of transmitting to the control device through the trunk line the detected values that were equal to or greater than the abnormal condition determination threshold values.

4. The gas monitoring method according to claim 3, wherein the abnormal condition determination threshold values are determined such that the abnormal condition determination threshold values become lower as the distance between the gas sensor and a target of leakage detection closest to the gas sensor becomes larger.

* * * * *